United States Patent [19]

Cross

[11] Patent Number: 5,160,330
[45] Date of Patent: Nov. 3, 1992

[54] MEDICO-SURGICAL COLLECTION BAG ASSEMBLIES

[75] Inventor: David E. Cross, Rustington, England

[73] Assignee: Smiths Industries Public Limited Company, London, England

[21] Appl. No.: 756,550

[22] Filed: Sep. 9, 1991

[30] Foreign Application Priority Data

Sep. 15, 1990 [GB] United Kingdom ............... 9020218

[51] Int. Cl.$^5$ ............................................. A61F 5/44
[52] U.S. Cl. .................................... 604/339; 604/338
[58] Field of Search ............................. 604/332–345

[56] References Cited

U.S. PATENT DOCUMENTS

| | | | |
|---|---|---|---|
| 3,021,843 | 2/1962 | Perry | 604/339 |
| 4,710,182 | 12/1987 | Bryson | 604/339 |
| 4,772,279 | 9/1988 | Brooks et al. | 604/339 |
| 4,775,374 | 10/1988 | Cilento et al. | 604/344 |
| 4,786,284 | 11/1988 | Silber | 604/339 |

FOREIGN PATENT DOCUMENTS

| | | |
|---|---|---|
| 0213721 | 3/1987 | European Pat. Off. . |
| 0235563 | 9/1987 | European Pat. Off. . |
| 0259184 | 3/1988 | European Pat. Off. . |
| 0270400 | 6/1988 | European Pat. Off. . |
| 0276043 | 7/1988 | European Pat. Off. ............. 604/338 |
| 2110361 | 2/1971 | Fed. Rep. of Germany ...... 604/338 |
| 1217406 | 12/1970 | United Kingdom . |
| 1274382 | 5/1972 | United Kingdom . |
| 1455784 | 11/1976 | United Kingdom . |
| 1568860 | 6/1980 | United Kingdom . |
| 1571986 | 7/1980 | United Kingdom . |
| 1579875 | 11/1980 | United Kingdom . |
| 1583027 | 1/1981 | United Kingdom . |
| 2115288 | 9/1983 | United Kingdom . |
| 2147810 | 5/1985 | United Kingdom . |
| 2148120 | 5/1985 | United Kingdom . |
| 2148716 | 6/1985 | United Kingdom . |
| 2153683 | 8/1985 | United Kingdom . |
| 2158719 | 11/1985 | United Kingdom . |
| 2163350 | 2/1986 | United Kingdom . |
| 2163959 | 3/1986 | United Kingdom . |
| 2172204 | 9/1986 | United Kingdom . |
| 2173403 | 10/1986 | United Kingdom . |
| 2179556 | 3/1987 | United Kingdom . |
| 2183481 | 6/1987 | United Kingdom . |
| 2190841 | 12/1987 | United Kingdom . |
| 2193097 | 2/1988 | United Kingdom . |
| 2193098 | 2/1988 | United Kingdom . |
| 2193439 | 2/1988 | United Kingdom . |
| 2193893 | 2/1988 | United Kingdom . |
| 2196257 | 4/1988 | United Kingdom . |
| 2198953 | 6/1988 | United Kingdom . |
| 2198954 | 6/1988 | United Kingdom . |
| 2201345 | 9/1988 | United Kingdom . |
| 2201346 | 9/1988 | United Kingdom . |
| 2201347 | 9/1988 | United Kingdom . |
| 2205041 | 11/1988 | United Kingdom . |
| 2206801 | 1/1989 | United Kingdom . |
| 2215212 | 9/1989 | United Kingdom . |

Primary Examiner—David Isabella
Assistant Examiner—R. Clark
Attorney, Agent, or Firm—Pollock, VandeSande and Priddy

[57] ABSTRACT

A two-part ostomy bag assembly has a patient fitment comprising a plate with an adhesive rear surface adhered on the skin around with stoma. The front surface of the plate is of PVC and non-adhesive. An annular flange with a rear surface of PVC is welded around its inner edge to the plate, leaving its outer edge free. The bag itself is w.c. disposable, having an adhesive disc secured to the inside wall of the bag around its opening which, in use, is secured to the front surface of the flange on the patient fitment.

13 Claims, 2 Drawing Sheets

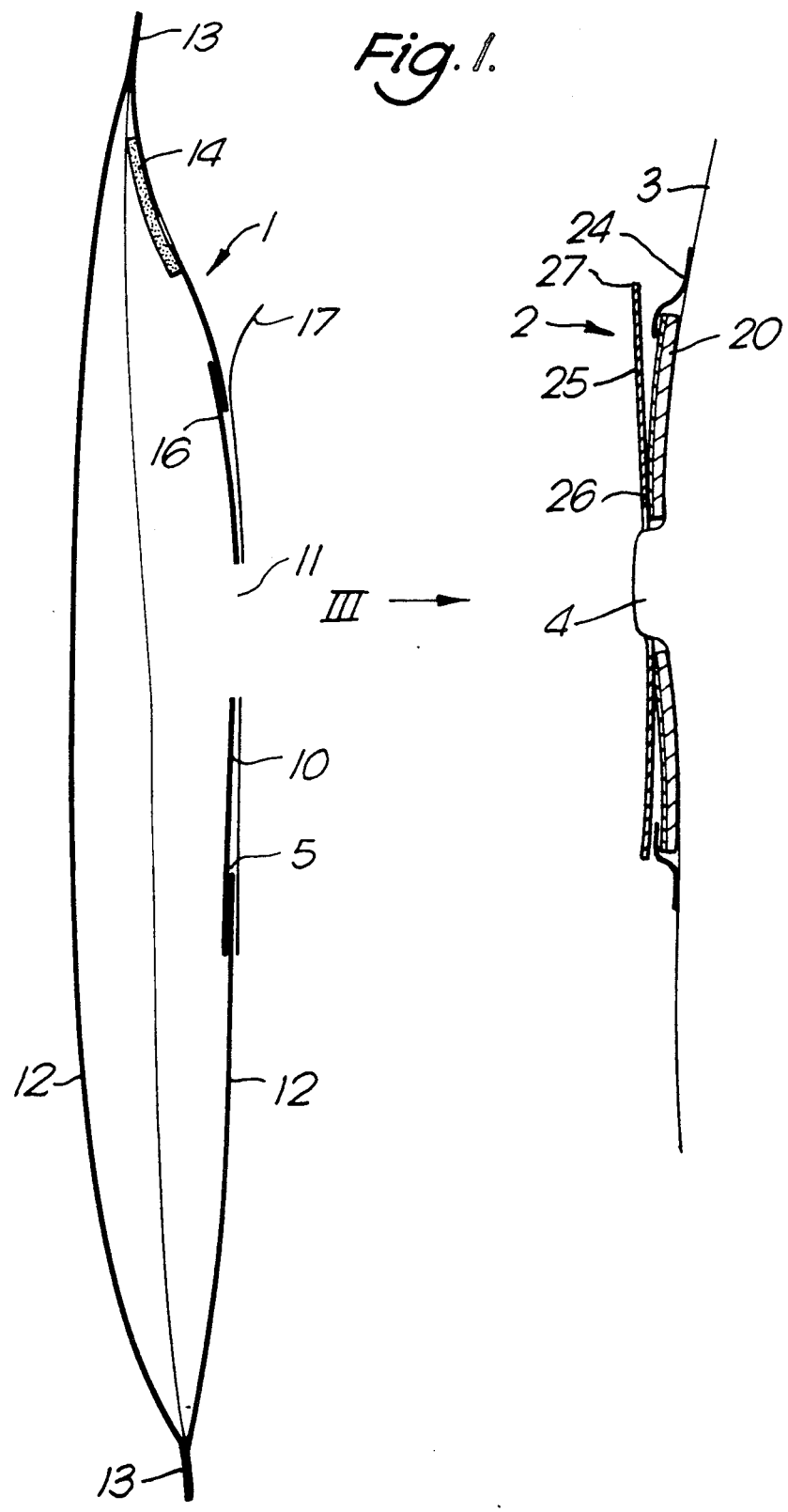

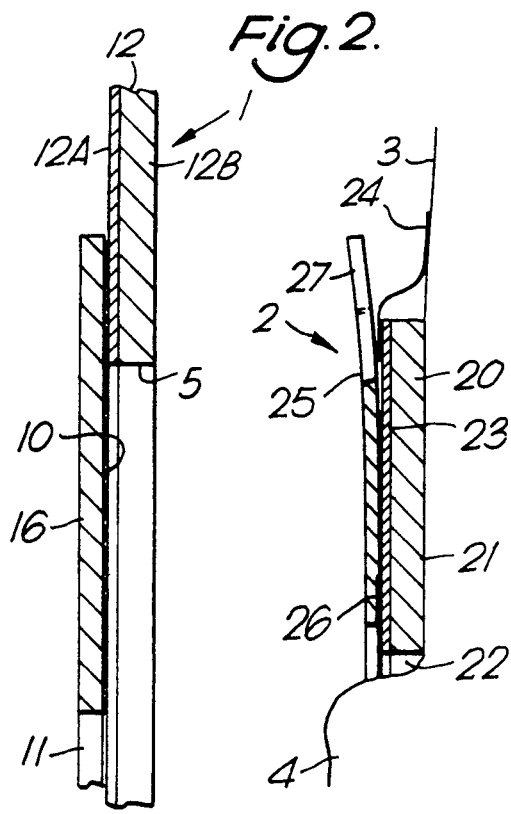
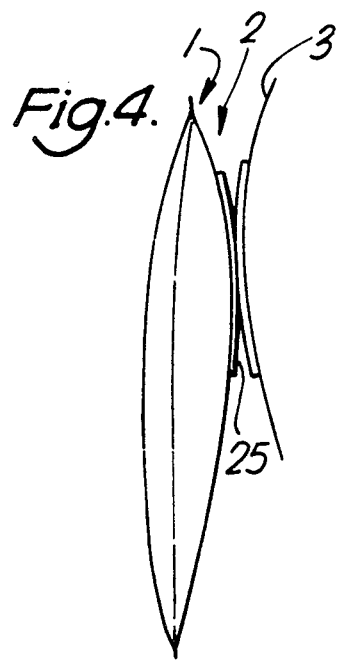
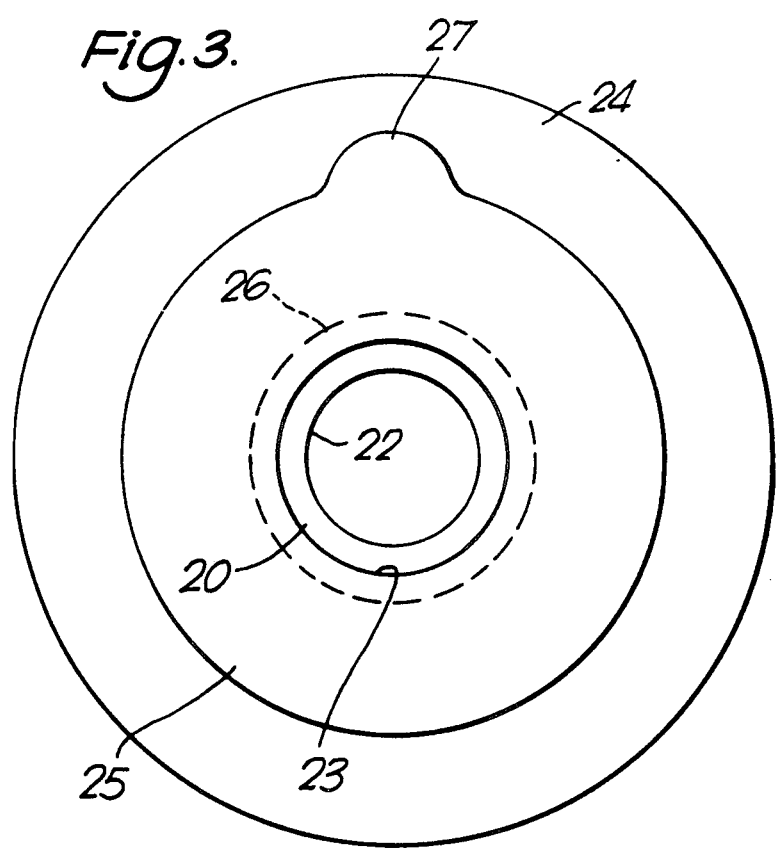

MEDICO-SURGICAL COLLECTION BAG ASSEMBLIES

BACKGROUND OF THE INVENTION

This invention relates to medico-surgical collection bag assemblies.

The invention is more particularly concerned with two-part ostomy bag assemblies and the like, having a bag that is removable from a fitment attached to the user's skin around a stoma or other discharge outlet.

Ostomy bags are used to collect fecal matter discharged from a surgically made stoma in the patient's abdomen. In one form of bag, the opening to the bag is provided with an adhesive ring which is used to secure the bag directly to the patient's skin around the stoma. The two-part ostomy bag assembly differs from this in that a fitment is adhered to the user's skin; the bag is a separate component, being coupled to the patient fitment in a releasable manner, usually by means of a relatively rigid coupling member on the bag. The bag is removed and disposed of when necessary by uncoupling from the fitment which remains in place to receive a new bag. The fitment can remain in place for several days before it also needs to be removed. Various forms of two-part assemblies have been proposed. These generally include mating rigid or semi-rigid coupling rings on the bag and fitment. Examples of such bag assemblies are described in EP0259184A, EP 0270400A, EP 0213721A, U.S. Pat. No. 4,775,374, GB 1455784, GB 1217406, GB 1568860, GB 1571986, GB 1579875, GB 1583027, GB2115288A, GB 2147810A, GB 2148120A, GB 2148716A, GB 2153683A, GB 2158719A, GB 2163350A, GB 2163959A, GB 2172204A, GB 2173403A, GB 2179556A, GB 2183481A, GB 2190841A, GB 2193097A, GB 2193098A, GB 2193439A, GB 2193893A, GB 2196257A, GB 2198953A, GB 2198954A, GB 2201345A, GB 2201346, GB 2201347A, GB 2205041A, GB 2206801A GB 2215212A. These forms of assembly suffer from various disadvantages since they are either difficult for the patient to use, or cause discomfort during coupling or uncoupling. The difficulty of coupling and uncoupling previous assemblies can sometimes disturb the seal of the body-worn fitment with the skin and lead to leakage. The coupling rings also mean that the assemblies are relatively bulky and obtrusive and may not flex with movement of the anatomy, leading to discomfort.

It has been proposed in GB 2225956A, to have a patient fitment with a planar front surface and to secure the bag to the fitment by means of an adhesive flange on the bag. A somewhat similar bag assembly is also sold by Eschmann Bros. & Walsh Limited under the trade mark Beta. Such assemblies have several advantages in that they can have very low profiles making them unobtrusive. They can be coupled and uncoupled easily without discomfort. They also lend themselves to use with w.c. disposable bags because the bag lacks any rigid coupling ring which could provide an obstruction to flushing. The difficulty with assemblies of these kinds is that, although they will provide a secure attachment to a flat surface, where the patient is fatter and the stoma is located on a convex part of the anatomy, there can be a tendency for a patient fitment to peel away from the skin, especially as the bag fills and becomes heavier. The problem is aggravated if the patient has skin folds in the region of the stoma. This problem could be reduced by making the patient fitment more flexible so that it conforms more readily to the anatomy but the problem is then transferred to the adhesive connection of the bag to the patient fitment, increasing the tendency of the patient fitment to separate from the bag. Where the patient fitment is flexible, it may wrinkle, especially with movement of the patient, making secure attachment to the patient fitment unreliable.

BRIEF SUMMARY OF THE INVENTION

It is an object of the present invention to provide a two-part collection bag assembly that can be used to alleviate these difficulties.

According to one aspect of the present invention there is provided a medico-surgical collection bag assembly for body waste products comprising a fitment which is arranged to be secured to the user around a body waste opening, and a collection bag which can be attached to the fitment in sealing engagement and released therefrom, the fitment including a flexible plate having an adhesive surface arranged to adhere on its rear side to the user's skin and an annular, planar flange member attached close to its inner edge to the plate, the flange member being unattached to the plate radially outwardly of the inner edge of the flange member, the flange member having a non-adhesive planar front surface, and the collection bag having an adhesive region around an opening to the bag that is adapted to adhere to the planar front surface of the flange member such that the plate can conform to the surface of the user's skin without substantially deforming the flange member.

The flange member is preferably of substantially circular shape. The adhesive region on the collection bag may have a smaller external diameter than that of the flange member. The flange member may have a tab projecting radially therefrom. The flexible plate may have a forward surface of PVC and the flange member a rear surface of PVC. The flange member may have a forward surface of polyethylene. The flange member is preferably attached to the plate by welding. The flange member is preferably uninterrupted by surface formations on its forward surface and may have a diameter substantially the same as that of the flexible plate. The adhesive surface of the flexible plate may be provided by a hydrophilic polymer in a support matrix of a hydrophobic polymer. The fitment may include a ring of an adhesive microporous material which overlaps the edge of the flexible plate and is in use secured to the user's skin.

The collection bag may be w.c. disposable. The adhesive region on the collection bag is preferably provided by an adhesive disc secured to the inside surface of a wall of the bag.

A two-part ostomy bag assembly in accordance with the present invention, will now be described, by way of example, with reference to the accompanying drawings.

BRIEF DESCRIPTION OF THE DRAWINGS

FIG. 1 is a side elevation view of the assembly;

FIG. 2 shows a part of the assembly in section to a larger scale;

FIG. 3 is a view of a part of the assembly along the line III in FIG. 1; and

FIG. 4 illustrates the assembly in use.

DESCRIPTION OF THE PREFERRED EMBODIMENTS

With reference to FIG. 1, the assembly comprises a w.c. disposable ostomy bag 1 and a user or body fitment 2 that is secured to the skin 3 of the user around a stoma 4. The bag 1 is provided with an adhesive region 10 around its opening 11 that can be secured to the fitment 2 and removed from it when necessary, leaving the fitment in position on the user.

With reference now also to FIGS. 2 and 3, the bag 1 has two flexible plastics sheets 12 of a w.c. disposable material which are welded together around their edge 13 to form the walls of a bag that is sealed apart from its opening 11 and an optional filtered flatus vent 14. The material used to form the sheets 12 may be of the kind used in the ostomy bag sold by Eschmann Bros. & Walsh Limited under the trade mark SYMPHONY. The material comprises a thin, water-resistant layer 12A that is presented inwardly to the contents of the bag and a thicker outer layer 12B that is broken up or dispersed in turbulent cold water so that the inner layer can collapse or break up without providing an obstacle to flushing. A circular aperture 5, about 72 mm in diameter, is formed in the sheet 12 which, in use, is towards the body of the user.

The adhesive region 10 is formed on the body side surface of a circular disc 16 which is about 93 mm in diameter. The disc 16 is of a flexible plastics material which is slightly less flexible than the walls 12 of the bag 1. The disc 16 is located internally of the bag with its outer edge being adhered to the inside surface of the wall 12 around the edge of the aperture 5. The aperture 11 of the bag is provided by a central aperture in the disc 16 which is chosen to be slightly larger than the user's stoma. Before use, the adhesive region 10 of the disc 16, which is presented outwardly of the bag, is protected by a removable release sheet 17.

The user fitment 2 includes a flexible plate 20 having an adhesive layer 21 on its rear surface formed of a hydrophilic polymer in a support matrix of a hydrophobic polymer, such as SEEL-A-PEEL (a Registered Trade Mark of Eschmann Bros. & Walsh Limited). The plate 20 is circular being about 80 mm in diameter with a central aperture 22 selected in size according to the size of the user's stoma 4. Prior to use, the rear, body side of the adhesive layer 21 is protected by a release sheet (not shown).

The plate 20 also includes a film 23 of plasticized PVC laminated to the adhesive layer 21, and an annular ring 24 of a microporous adhesive material attached to the forward surface of the film 23 around the outer edge of the adhesive layer 21 to overlap it by about 18 mm around its circumference. The microporous ring 24 is thin compared with the layer 21 and is adhesive on its rear surface which serves to adhere it to the film 23 and to the user's skin 3 around the plate 20 so as to reduce the risk of the adhesive layer 21 peeling away from the skin around its outer edge. Prior to use, the rear, adhesive surface of the microporous ring 24, where it projects beyond the adhesive layer 21, is protected by a release sheet (not shown).

The fitment is completed by a transparent floating annular flange 25 of circular shape which is made from a flat, planar laminate of PVC and polyethylene. The flange 25 is planar and flat, being uninterrupted by any surface formation on its forward surface. The flange 25 has substantially the same external diameter as the adhesive layer 21 and has an internal diameter slightly larger than the aperture 22 in the plate 20. The thickness and nature of the flange 25 is such that it is bendable but is more resilient than the plate 20, so that it tends to retain a substantially flat shape. The PVC side of the flange 25 is presented towards the user and the polyethylene side is presented towards the bag 1.

The flange 25 is secured to the plate 20 by welding a narrow annular region 26 around the central aperture of the flange to the plate and, more particularly, by welding the PVC side of the flange to the PVC film 23 of the plate. The flange 25 is unattached to the plate 20 at locations radially outwards of the welded region 26, the PVC film 23 covering the layer 21 ensuring the flange 25 does not adhere to the plate.

In use, the release sheet is removed from the rear surface of the plate 20 and this is pressed into position onto the skin around the user's stoma 4 which usually projects through the opening 22 in the plate. The release sheet is removed from the microporous ring 24 which is then smoothed down onto the skin around the plate 20. The user then removes the release sheet 17 from the adhesive region 10 of the bag 1 and holds this up to the flange 25. The adhesive region 10 is pressed into contact with the flange 25 which the user can do by putting a thumb behind the flange and by squeezing the bag into contact with the flange with the index finger of the same hand. The diameter of the adhesive region 10 exposed around the opening of the bag is slightly less than the diameter of the flange 25 so that, if there is any misalignment of the bag on the fitment, there is less risk that any adhesive on the bag will be exposed beyond the flange. It also helps removal of the bag from the fitment; this can also be facilitated by the provision of a radially projecting tab 27 on the flange which enables the user to grip the flange more readily.

The flange 25 tends to retain a relatively flat shape because it is only attached at a central region. If the fitment is applied to a user who is obese, and whose anatomy in the region of the stoma is convex, the plate 20 will assume the shape of the anatomy but the flange 25 will remain relatively flat. This has several advantages which are particularly useful in assemblies of the present kind which are connected adhesively. Firstly, the flange 25 does not add to the stiffness of the adhesive plate so that the plate can remain flexible and conform closely to the user's anatomy with consequently a reduced risk of separation from the skin. Secondly, any force pulling the top of the bag down is accommodated by bending down the upper part of the flange 25 rather than by peeling the bag away from the fitment, as would be the case if the bag were attached directly to the plate 20. Furthermore, the relatively flat nature of the flange ensures that there is a secure adhesive bond between the bag and the flange compared with what would be the case if the flange assumed the convex shape of the user's anatomy. Preferably, the flexibility of the flange is sufficient that it is deformed slightly by the weight of the bag and its contents, to a concave shape, as shown in FIG. 4.

When the bag 1 is full, it is removed by peeling away from the flange 25, leaving the fitment 2 in position on the skin. Because the flange 25 is flat and non-adhesive it can be readily cleaned and does not collect waste material. After cleaning, a fresh bag is adhered to the fitment in the manner described above.

The adhesive connection of the bag on the fitment enables an assembly to be produced that has a lower profile than assemblies involving mating coupling rings. This enables the assembly to be less conspicuous under clothing and to be more comfortable. The simple construction of the assembly enables it to be manufactured accurately at low cost.

It will be appreciated that different materials and sizes could be used without departing from the invention, and particularly, that the bag need not be w.c. disposable.

The adhesive region around the bag opening could be provided on a flange which is attached to the bag centrally and unattached around its outer edge.

What I claim is:

1. In a medico-surgical collection bag assembly for body waste products of the kind comprising a fitment including a flexible plate with an adhesive rear surface that adheres to the user's skin around a body waste opening, and a collection bag that is attachable to and releasable from the fitment, the improvement wherein the fitment includes an annular, planar floating flange member attached to said plate at a rear surface of said flange member over a region close to an inner edge of said annular flange member, said flange member being unattached to the plate radially outwardly of said region close to the inner edge of the flange member, the flange member having a nonadhesive planar front surface, the collection bag having an adhesive region around an opening to the bag that adheres directly to the planar front surface of the flange member over at least that part of the flange member radially outwardly of the said region close to the inner edge, and said flange member being bendable and more resilient than the plate such that the plate can conform to the surface of the user's skin without substantially deforming the flange member from a relatively flat shape but the flange member can be bent by the weight of the bag and its contents before the adhesive on the bag peels away from the flange member.

2. An assembly according to claim 1, wherein the flange member is of substantially circular shape.

3. An assembly according to claim 1, wherein the adhesive region on the collection bag has a smaller external diameter than that of the flange member.

4. An assembly according to claim 1, wherein the flange member has a tab projecting radially therefrom.

5. An assembly according to claim 1, wherein the flexible plate has a forward surface of PVC, and wherein the flange member has a rear surface of PVC.

6. An assembly according to claim 1, wherein the flange member has a forward surface of polyethylene.

7. An assembly according to claim 1, wherein the flange member is attached to the plate by welding.

8. An assembly according to claim 1, wherein the flange member is uninterrupted by surface formations on its forward surface.

9. An assembly according to claim 1, wherein the diameter of the flange member is substantially the same as that of the flexible plate.

10. An assembly according to claim 1, wherein the adhesive surface of the flexible plate is provided by a hydrophilic polymer in a support matrix of a hydrophobic polymer.

11. An assembly according to claim 1, wherein the fitment includes a ring of an adhesive microporous material which overlaps the edge of the flexible plate and is in use secured to the user's skin.

12. An assembly according to claim 1, wherein the collection bag is w.c. disposable.

13. An assembly according to claim 1, wherein the adhesive region on the collection bag is provided by an adhesive disc secured to the inside surface of a wall of the bag.

* * * * *